(12) United States Patent
Bui

(10) Patent No.: US 8,603,444 B2
(45) Date of Patent: *Dec. 10, 2013

(54) COSMETIC COMPOSITIONS CONTAINING A BLOCK COPOLYMER, A TACKIFIER AND A HIGH VISCOSITY ESTER

(75) Inventor: Hy Si Bui, Piscataway, NJ (US)

(73) Assignee: L'Oréal (FR)

( * ) Notice: Subject to any disclaimer, the term of this patent is extended or adjusted under 35 U.S.C. 154(b) by 897 days.

This patent is subject to a terminal disclaimer.

(21) Appl. No.: 11/972,161

(22) Filed: Jan. 10, 2008

(65) Prior Publication Data

US 2008/0171007 A1    Jul. 17, 2008

Related U.S. Application Data

(60) Provisional application No. 60/880,281, filed on Jan. 12, 2007.

(51) Int. Cl.
*A61K 8/18* (2006.01)

(52) U.S. Cl.
USPC .......................................... 424/64; 424/78.03

(58) Field of Classification Search
USPC ............ 524/109, 110, 111; 424/63, 64, 78.03
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speier et al. | |
| 3,723,566 A | 3/1973 | Thompson et al. | |
| 4,116,924 A | 9/1978 | Peabody | |
| 4,322,400 A | 3/1982 | Yuhas | |
| 4,492,428 A | 1/1985 | Levy | |
| 4,822,852 A | 4/1989 | Wittmann et al. | |
| 4,913,235 A | 4/1990 | Harris et al. | |
| 5,262,505 A | 11/1993 | Nakashima et al. | |
| 5,272,241 A | 12/1993 | Lucarelli et al. | |
| 5,294,438 A | 3/1994 | Chang et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,492,945 A | 2/1996 | Morita et al. | |
| 5,538,793 A | 7/1996 | Inokuchi et al. | |
| 5,567,428 A | 10/1996 | Hughes | |
| 5,618,883 A | 4/1997 | Plamthottam et al. | |
| 5,648,066 A | 7/1997 | Stepniewski | |
| 5,653,968 A | 8/1997 | Carballada et al. | |
| 5,656,286 A | 8/1997 | Miranda et al. | |
| 5,690,918 A | 11/1997 | Jacks et al. | |
| 5,725,882 A | 3/1998 | Kumar et al. | |
| 5,726,220 A | 3/1998 | Tokushige et al. | |
| 5,756,568 A | 5/1998 | Morita et al. | |
| 5,837,223 A | 11/1998 | Barone et al. | |
| 5,843,407 A | 12/1998 | El-Nokaly et al. | |
| 5,945,471 A | 8/1999 | Morita et al. | |
| 5,969,172 A | 10/1999 | Nye | |
| 5,985,297 A | 11/1999 | Mellul et al. | |
| 6,024,822 A * | 2/2000 | Alper et al. ................. | 156/273.3 |
| 6,103,250 A | 8/2000 | Brieva et al. | |
| 6,177,091 B1 | 1/2001 | Bara et al. | |
| 6,200,581 B1 | 3/2001 | Lin et al. | |
| 6,258,347 B1 | 7/2001 | Sakuta et al. | |
| 6,348,152 B1 | 2/2002 | Kawahara et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,376,078 B1 | 4/2002 | Inokuchi | |
| 6,403,070 B1 | 6/2002 | Pataut et al. | |
| 6,423,324 B1 | 7/2002 | Murphy et al. | |
| 6,426,062 B1 | 7/2002 | Chopra et al. | |
| 6,433,163 B1 | 8/2002 | Ho | |
| 6,451,295 B1 | 9/2002 | Cai et al. | |
| 6,503,491 B2 | 1/2003 | Guenin et al. | |
| 6,517,818 B1 | 2/2003 | Golz-Berner et al. | |
| 6,524,598 B2 | 2/2003 | Sunkel et al. | |
| 6,541,017 B1 | 4/2003 | Lemann et al. | |
| 6,544,642 B2 | 4/2003 | Cinelli et al. | |
| 6,566,026 B2 | 5/2003 | Watanabe et al. | |
| 6,682,748 B1 | 1/2004 | De La Poterie et al. | |
| 6,916,464 B2 | 7/2005 | Hansenne et al. | |
| 6,958,155 B2 | 10/2005 | Lu et al. | |
| 6,960,339 B1 | 11/2005 | Ferrari | |
| 7,078,026 B2 | 7/2006 | Ferrari et al. | |
| 7,083,800 B1 | 8/2006 | Terren et al. | |
| 7,321,011 B2 | 1/2008 | Lu et al. | |
| 7,329,699 B2 | 2/2008 | Liew et al. | |
| 7,884,158 B2 | 2/2011 | Bui et al. | |
| 7,887,786 B2 | 2/2011 | Tournilhac et al. | |

(Continued)

FOREIGN PATENT DOCUMENTS

| | | |
|---|---|---|
| CA | 2278685 A1 | 8/1998 |
| CN | 1246787 A | 3/2000 |

(Continued)

OTHER PUBLICATIONS

U.S. Appl. No. 11/972,143, filed Jan. 10, 2008, Bui et al.
U.S. Appl. No. 11/972,839, filed Jan. 11, 2008, Hy Si Bui.
U.S. Appl. No. 11/972,102, filed Jan. 10, 2008, Florentina Pavel.
Eric A. Grulke, "Solubility Parameter Values", Polymer Handbook 3rd edition, edited by J. Brandrup and E. H. Immergut, Chapter VII, pp. 519-559, A Wiley-Interscience Publication, John Wiley & Sons, 1989.
Charles M. Hansen: "The three-dimensional solubility parameters", Journal of Paint Technology, vol. 39, No. 505 (Feb. 1967).
McCutcheon's, Detergents and Emulsifiers, North American Edition (2003), Allured Publishing Corporation.
Chinese Communication dated Mar. 5, 2010 as received in corresponding Chinese application No. 200710128891.9.

(Continued)

*Primary Examiner* — Peter D Mulcahy
(74) *Attorney, Agent, or Firm* — Lerner, David, Littenberg, Krumholz & Mentlik, LLP

(57) ABSTRACT

A method of making up keratinous substrates involving applying onto the keratinous substrates a composition containing a) a block copolymer, b) a tackifier, c) a wax, d) a liquid fatty phase, e) a high viscosity ester, and f) optionally, a colorant.

20 Claims, No Drawings

(56) References Cited

U.S. PATENT DOCUMENTS

| | | |
|---|---|---|
| 2002/0028223 A1 | 3/2002 | Vatter et al. |
| 2002/0031488 A1 | 3/2002 | Kanji et al. |
| 2002/0031968 A1 | 3/2002 | Hamaguchi et al. |
| 2002/0048557 A1 | 4/2002 | Cai et al. |
| 2002/0051758 A1 | 5/2002 | Cai et al. |
| 2002/0114773 A1 | 8/2002 | Kanji et al. |
| 2003/0035944 A1 | 2/2003 | Blackwell |
| 2003/0039620 A1 | 2/2003 | Rodriguez et al. |
| 2003/0059448 A9 | 3/2003 | Kanji et al. |
| 2003/0068344 A1 | 4/2003 | Ferrari et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu |
| 2003/0235553 A1 | 12/2003 | Lu et al. |
| 2004/0001799 A1 | 1/2004 | Lu et al. |
| 2004/0076594 A1 | 4/2004 | Legrand |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0137028 A1 | 7/2004 | de la Poterie |
| 2004/0197285 A1 | 10/2004 | Van Dort |
| 2004/0223936 A1 | 11/2004 | Fecht et al. |
| 2004/0223989 A1 | 11/2004 | Auguste et al. |
| 2004/0234612 A1 | 11/2004 | Blin et al. |
| 2005/0009989 A1 | 1/2005 | Liew et al. |
| 2005/0020769 A1 | 1/2005 | Lu et al. |
| 2005/0061435 A1 | 3/2005 | Everaerts et al. |
| 2005/0089492 A1 | 4/2005 | Lu et al. |
| 2005/0158260 A1 | 7/2005 | Ferrari et al. |
| 2005/0228115 A1 | 10/2005 | Auguste et al. |
| 2005/0245673 A1 | 11/2005 | Ferrari et al. |
| 2005/0287105 A1 | 12/2005 | Blin et al. |
| 2006/0029560 A1 | 2/2006 | Blin |
| 2006/0030685 A1* | 2/2006 | Passade Boupat et al. ... 526/319 |
| 2006/0099168 A1* | 5/2006 | Corzani et al. ............. 424/70.17 |
| 2006/0110345 A1 | 5/2006 | Lu et al. |
| 2006/0120983 A1 | 6/2006 | Blin et al. |
| 2006/0193801 A1 | 8/2006 | Blin et al. |
| 2006/0204470 A1 | 9/2006 | Tournilhac |
| 2007/0041920 A1* | 2/2007 | Blin et al. ........................ 424/64 |
| 2007/0041928 A1 | 2/2007 | Chen et al. |
| 2007/0053859 A1 | 3/2007 | Bui et al. |
| 2007/0142521 A1* | 6/2007 | Brahms et al. ................ 524/356 |
| 2007/0149703 A1 | 6/2007 | Caprasse et al. |
| 2007/0212317 A1 | 9/2007 | Atis et al. |
| 2007/0258923 A1 | 11/2007 | Bui et al. |
| 2007/0258924 A1 | 11/2007 | Bui et al. |
| 2007/0258925 A1 | 11/2007 | Bui et al. |
| 2007/0258932 A1 | 11/2007 | Bui et al. |
| 2007/0258933 A1 | 11/2007 | Bui et al. |
| 2007/0258934 A1 | 11/2007 | Bui et al. |
| 2008/0102049 A1 | 5/2008 | McDermott |
| 2008/0171006 A1 | 7/2008 | Bui et al. |
| 2008/0171007 A1 | 7/2008 | Bui |
| 2008/0171008 A1 | 7/2008 | Bui |
| 2008/0254076 A1 | 10/2008 | Ferrari et al. |
| 2010/0098648 A1 | 4/2010 | Yu |
| 2012/0219516 A1 | 8/2012 | Ramada et al. |

FOREIGN PATENT DOCUMENTS

| | | |
|---|---|---|
| CN | 1646656 A | 7/2005 |
| CN | 1761446 A | 4/2006 |
| EP | 0377447 A2 | 7/1990 |
| EP | 0693517 A1 | 1/1996 |
| EP | 1582203 A1 | 10/2005 |
| FR | 2765800 A1 | 1/1999 |
| FR | 2785530 A1 | 5/2000 |
| FR | 2842100 A1 | 1/2004 |
| FR | 2873030 A1 | 1/2006 |
| GB | 1348783 A | 3/1974 |
| JP | 60255713 A | 12/1985 |
| JP | 06-024969 | 2/1994 |
| JP | 2000178126 A | 6/2000 |
| JP | 2001097852 A | 4/2001 |
| JP | 2001507591 A | 6/2001 |
| JP | 2001511161 A | 8/2001 |
| JP | 2002097366 A | 4/2002 |
| JP | 2002528477 A | 9/2002 |
| JP | 2003516949 A | 5/2003 |
| JP | 2004035567 A | 2/2004 |
| JP | 2004115774 A | 4/2004 |
| JP | 2004256539 A | 9/2004 |
| JP | 2005225867 A | 8/2005 |
| JP | 2005528471 A | 9/2005 |
| JP | 2006028181 A | 2/2006 |
| JP | 2007297391 A | 11/2007 |
| JP | 2007532754 A | 11/2007 |
| JP | 2008512498 A | 4/2008 |
| JP | 2009521549 A | 6/2009 |
| WO | 9736573 A1 | 10/1997 |
| WO | 9824588 A1 | 6/1998 |
| WO | 0109239 A1 | 2/2001 |
| WO | 03087254 A | 10/2003 |
| WO | 03087254 A2 | 10/2003 |
| WO | 2004066918 A2 | 8/2004 |
| WO | WO 2005/100444 | 10/2005 |
| WO | 2007031872 A2 | 3/2007 |
| WO | 2007078825 A2 | 7/2007 |

OTHER PUBLICATIONS

Chinese Communication dated May 15, 2009 as received in corresponding Chinese application No. 200710128891.9.

Chinese Communication dated May 8, 2009 as received in corresponding Chinese application No. 200710128890.4.

Chinese Communication dated May 9, 2011 as received in corresponding Chinese application No. 200710128890.4.

Chinese Communication dated Nov. 17, 2010 as received in corresponding Chinese application No. 200710128891.9.

European Communication dated Apr. 24, 2008 as received in corresponding European application No. 07008772.1.

European Communication dated Mar. 16, 2010 as received in corresponding European Application No. 07008772.1.

European Communication dated Mar. 31, 2008 as received in corresponding European application No. 07008771.3.

European Search Report as received in corresponding European application No. 07008772.1, Feb. 18, 2008.

Factsheet—DOW CORNING 670 Fluid—Intellectual Property Statement—Apr. 14, 2005.

Hansen, Paint and Coating Testing Manual, 1995, Joseph V. Koleske Editor., pp. 383-404.

Japanese Communication dated Mar. 1, 2011 as received in corresponding Japanese application No. 2007-121913.

Japanese Communication dated Mar. 1, 2011 as received in corresponding Japanese Application No. 2007-121914.

Japanese Communication dated Nov. 17, 2009 as received in corresponding Japanese application No. 2007-121913.

Japanese Communication dated Nov. 17, 2009 as received in corresponding Japanese Application No. 2007-121914.

Silkflo Technical Sheet, http://www.in-cosmeticsasia.com/Exhibitorlibrary/205/Sellsheet_-Silkflo_new_Aug07 2.pdf, obtained online on Sep. 2, 2009.

Virginie Caprasse, Isabelle Van Reeth, Dow Corning S.A., Research Disclosure, A new silicone resin for personal care applications, Research Disclosure Database No. 486008, Published in Oct. 2004 (Eiectronic publication date: Sep. 10, 2004 ), Research Disclosure Journal, Kenneth Mason Publications Ud., The Book Barn, Westbourne, Hants. P010 8RS UK.

Zhang et al., J. Colloid Interface Science, 2003, 266, 339-345.

* cited by examiner

US 8,603,444 B2

COSMETIC COMPOSITIONS CONTAINING A BLOCK COPOLYMER, A TACKIFIER AND A HIGH VISCOSITY ESTER

STATEMENT OF RELATED APPLICATIONS

This application is a non-provisional application of, and claims benefit to, U.S. Provisional Application No. 60/880,281, filed Jan. 12, 2007.

BACKGROUND OF THE INVENTION

There have been many developments in connection with improving comfort, wear, shine and/or longevity of cosmetic compositions for the face, eye, lips nails or hair. Commercially available lip treatment compositions such as lip glosses and lipsticks possess a certain level of gloss or shine depending of their composition. Efforts have been made to improve shine/gloss through the use of silicone fluids but the wear of shine and wear of color leaves much to be desired. Generally, a composition with a high level of shine has poor wear and a long wear composition lacks shine. Therefore, it is an object of the present invention to provide a cosmetic composition which is comfortable to apply and wear, and has long lasting color and shine.

BRIEF SUMMARY OF THE INVENTION

A first aspect of the present invention is directed to a method of making up keratinous substrates involving applying onto the keratinous substrates a composition containing a) a block copolymer, b) a tackifier, c) a wax, d) a liquid fatty phase, e) a high viscosity ester, and f) optionally, a colorant.

A second aspect of the present invention is directed to a cosmetic composition comprising a) a block copolymer, b) a tackifier, c) a wax, d) a liquid fatty phase, e) a high viscosity ester, and f) optionally, a colorant.

It has been surprisingly discovered that the use of the above-disclosed cosmetic composition delivers a superior wear of color and a high level of shine.

DETAILED DESCRIPTION OF THE INVENTION

Other than in the operating examples, or where otherwise indicated, all numbers expressing quantities of ingredients and/or reaction conditions are to be understood as being modified in all instances by the term "about".

Block Copolymer

The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$" More particularly, the hard segment has a $T_g$ of 50° C. or more, whereas the soft segment has a $T_g$ of 20° C. or less. The glass transition temperature $T_g$ for the hard block can range from 50° C. to 150° C.; 60° C. to 125° C.; 70° C. to 120° C.; 80° C. to 110° C. The glass transition temperature $T_g$ for the soft segment of the block copolymer can range from 20° C. to −150° C.; 0° C. to −135° C.; −10° C. to −125° C.; −25° C. to −100° C. A more in depth explanation can be found in U.S. Pat. Nos. 5,294,438 and 6,403,070, the entire contents of which are hereby incorporated by reference.

One type of block copolymer which may be employed by the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

A particularly preferred block copolymer for use in the present invention is a combination of di-block and tri-block copolymers of styrene-ethylene/butylene-styrene, commercially available from Shell Chemical Company under trade name Kraton G1657M. It should be noted, however, that any thermoplastic elastomer of the block copolymer type having at least one soft and at least one hard segment may be used without departing from the spirit of the invention.

The block copolymer is present in the cosmetic composition in an amount ranging from greater than 0% to 20% by weight, based on the weight of the composition.

Tackifier

A substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter δ according to the Hansen solubility space is defined in the article "*Solubility Parameter Values*" by Eric A. Grulke in the work "*Polymer Handbook*" 3rd edition, Chapter VII, pages 519-559, the entire content of which is hereby incorporated by reference, by the relationship:

$$\delta=(d_D^2+d_P^2+d_H^2)^{1/2}, \text{ in which:}$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105 (1967), the entire content of which is hereby incorporated by reference.

The at least one tackifier used in the present invention will have a solubility parameter corresponding to δ and the block copolymer will have at least one segment whose solubility parameter corresponds to δ±2, preferably δ±1.7, more preferably δ±1.5, more preferably δ±1.3, more preferably δ±1.0, more preferably δ±0.7, more preferably 6±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.)

In some embodiments, the tackifier may have a softening point (Ring and Ball, as measured by ASTM E-28) of 80° C. to 150° C., preferably 100° C. to 130° C. In other embodiments the tackifier may be liquid and have an R and B softening point of between about −70° C. and 70° C.

In some embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred tackifier for use in the present invention is a hydrogenated hydrocarbon resin such, for example, a hydrogenated styrene/methyl styrene/indene copolymer, commercially available from Eastman under the tradename Regalite® R1100.

The tackifier is present in the cosmetic composition of the present invention in an amount ranging from greater than 0% to 60% by weight, based on the weight of the composition.

Waxes

The cosmetic compositions in accordance with the present invention also contain waxes. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

The waxes are present in the composition of the present invention in an amount of from greater than 0% to 40%, based on the weight of the composition.

Liquid Fatty Phase

The cosmetic composition of the present invention comprises a liquid fatty phase. The liquid fatty phase may contain at least one oil chosen from a volatile silicone oil, a volatile hydrocarbon oil, a non-volatile silicone oil, a non-volatile hydrocarbon oil, and mixtures thereof.

Suitable volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane, and their mixtures. Preferably, the volatile silicone oils have a flash point of at least 40° C.

Suitable volatile hydrocarbon oils include, but are not limited to, those having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile hydrocarbon oils have a flash point of at least 40° C.

Suitable non-volatile silicone oils that may be used include, but are not limited to, linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane.

Suitable non-volatile hydrocarbon oils which can be used in the compositions of the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R^2COOR^3$ in which $R^2$ represents a linear or branched higher fatty acid residue containing from 1 to 40 carbon atoms, including from 7 to 19 carbon atoms, and $R^3$ represents a branched hydrocarbon-based chain containing from 1 to 40 carbon atoms, including from 3 to 20 carbon atoms, with $R^2+R^3 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;
$C_8$ to $C_{26}$ fatty alcohols, for instance oleyl alcohol; and mixtures thereof.

The liquid fatty phase is present in the composition of the present invention in an amount of from greater than 0% to 80% by weight, such as 10% to 80% by weight, such as 20% to 70% by weight, such as 30% to 60% by weight, based on the weight of the composition.

High Viscosity Ester

The cosmetic composition of the present invention also contains a high viscosity ester. Examples thereof include, but not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are $C_{18}$ mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about 1 oleic acid moiety in the molecule. Other materials may include cottonseed oil or soybean oil fatty acid esters of sucrose.

A preferred high viscosity ester for use in the present invention is sucrose acetate isobutyrate. One example of a suitable sucrose acetate isobutyrate compound is SAIB-100®, commercially available from Eastman®, Kingsport, Tenn. It has a viscosity of about 100,000 cps at 30° C. and a refractive index of about 1.5 at 20° C.

The high viscosity ester is present in the composition of the invention in an amount of from greater than 0% to 50% by weight, based on the weight of the composition.

Colorant

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

Alkyl Silsesquioxane Resin

In cases where more wear and adhesion are desired, the composition of the present invention may also contain an alkyl silsesquioxane resin. Alkyl silsesquioxane resins are silsesquioxane homopolymers and/or copolymers having an average siloxane unit of the general formula $R^1_n SiO_{(4-n)/2}$, wherein each $R^1$ is independently chosen from a hydrogen atom and a $C_1$-$C_{10}$ alkyl group, wherein more than 80 mole % of $R^1$ represent a $C_3$-$C_{10}$ alkyl group, n is a value of from 1.0 to 1.4, and more than 60 mole % of the copolymer comprises $R^1 SiO_{3/2}$ units.

Preferably, the silsesquioxane resin used is one where $R^1$ is a $C_1$-$C_{10}$, preferably a $C_1$-$C_4$ alkyl group, and more preferably a propyl group. One example of an alkyl silsesquioxane resin suitable for use in the present invention is a propyl silsesquioxane resin commercially available from Dow-Corning as Dow Corning® 670 Fluid.

The alkyl silsesquioxane resin may be present in an amount ranging from greater than 0% to 50% by weight, based on the weight of the composition.

Alkyl Silsesquioxane Wax

The cosmetic composition of the present invention may also contain alkyl silsesquioxane waxes. The alkyl silsesquioxane waxes for use in the present invention have been disclosed in WO2005/100444, the entire contents of which is hereby incorporated by reference. This particular kind of resin wax is derived from an alkyl silsesquioxane resin modified to contain at least two distinct hydrocarbon groups within the polymer. The first hydrocarbon group has from 1 to 8 carbon atoms, and the second hydrocarbon group has from 9 to 40 carbon atoms.

The alkyl silsesquioxane wax comprises at least 40 mole % of siloxy units having the formula $(R^4_2 R^5 SiO_{1/2})_x (R^6 SiO_{3/2})_y$, where x and y have a value of 0.05 to 0.95, $R^4$ is an alkyl group having from 1 to 8 carbon atoms, an aryl group, a carbinol group, or an amino group, $R^5$ is a monovalent hydrocarbon having 9 to 40 carbon atoms, $R^6$ is a monovalent hydrocarbon group having 1 to 8 carbon atoms or an aryl group. As used herein, x and y represent the mole fraction of $(R^4_2 R^5 SiO_{1/2})$ and $(R^6 SiO_{3/2})$ siloxy units relative to each other present in the silsesquioxane wax. Thus, the mole fraction of $(R^4_2 R^5 SiO_{1/2})$ and $(R^6 SiO_{3/2})$ siloxy units each can independently vary from 0.05 to 0.95. Preferably $R^4$ is a methyl, $R^5$ is a C30-C45 alkyl, and $R^6$ is a propyl.

Typically, the value of x is 0.05 to 0.95, or alternatively, 0.2 to 0.8, the value of y is 0.05 to 0.95, alternatively 0.2 to 0.8. However, the combination of $(R^4_2 R^5 SiO_{1/2})$ and $(R^6 SiO_{3/2})$ siloxy units present must total at least 40 mole %, alternatively 60 mole %, or alternatively 90 mole % of all siloxy units present in the alkyl silsesquioxane wax. The alkyl silsesquioxane wax may be a liquid, soft solid, or solid material at room temperature.

The molecular weights of the alkyl silsesquioxane wax are not restricted, but typically the number average molecular weight ($M_N$) ranges from 750 to 10,000, such as from 1,000 to 5,000.

The alkyl silsesquioxane wax may be present in the cosmetic composition of the present invention in an amount ranging from greater than 0% to 30% by weight, based on the weight of the composition.

Emulsifiers

The composition of the present invention may contain at least one compound useful as an emulsifier. Suitable emulsifiers that can be used according to the present invention include, but are not limited to, nonionic, cationic, anionic, and zwitterionic emulsifiers. Suitable emulsifiers according to the present invention include, but are not limited to, acyl lactylates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps, alkoxylated polydimethylsiloxanes, and mixtures thereof.

Additional compounds suitable as emulsifiers include, but are not limited to, emulsifying crosslinked siloxane elastomers such as Dimethicone/PEG-10/15 Crosspolymer available as KSG-210, Dimethicone/Polyglycerin-3 Crosspolymer available as KSG 710, Lauryl PEG-15 Dimethicone/Vinyl Dimethicone Crosspolymer available as KSG-31, PEG-12 Dimethicone Crosspolymer, available as DC 9011. In one embodiment, the compound useful as an emulsifier is Dimethicone/PEG-10/15 Crosspolymer. For examples of other suitable emulsifiers that can be used according to the present invention, see, for example, McCutcheon's, Detergents and Emulsifiers, North American Edition (2003), Allured Publishing Corporation, the entire contents of which are hereby incorporated by reference.

The emulsifier may be present in the cosmetic composition of the present invention in an amount ranging from greater than 0% to 10% by weight, based on the weight of the composition.

Non-Emulsifying Silicone Elastomers

The composition of the present invention may contain non-emulsifying silicone elastomers The term "non-emulsifying" defines silicone elastomers not containing a hydrophilic chain, such as polyoxyalkylene or polyglycerolated units.

The non-emulsifying silicone elastomer is preferably an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

The elastomeric crosslinked organopolysiloxanes may be conveyed in the form of a gel consisting of an elastomeric organopolysiloxane included in at least one hydrocarbon-based oil and/or one silicone oil. The elastomeric crosslinked organopolysiloxanes may also be in powder form.

Suitable non-emulsifying silicone elastomers for use in the composition of the present invention include, but are not limited to, those sold under the names "DC 9040®", "DC 9041®", "DC 9509®", "DC 9505®" and "DC 9506®" by the company Dow Corning, and KSG-6®, KSG-8®, KSG-10®, KSG-14®, KSG-15®, and KSG-16® by the company Shin-Etsu; SFE-168® and SFE-839® available from GE Silicones; and Gransil SR-SYC® available from Grant Industries.

The non-emulsifying silicone elastomer may also be in the form of elastomeric crosslinked organopolysiloxane powder coated with silicone resin, especially with silsesquioxane resin, as described, for example, in patent U.S. Pat. No. 5,538,793, the entire content of which is herein incorporated by reference. Such elastomers are sold under the names "KSP-100®", "KSP-101®", "KSP-102®", "KSP-103®", "KSP-104®" and "KSP-105®" by the company Shin-Etsu.

Other elastomeric crosslinked organopolysiloxanes in the form of powders include hybrid silicone powders functionalized with fluoroalkyl groups, sold especially under the name "KSP-200®" by the company Shin-Etsu; hybrid silicone powders functionalized with phenyl groups, sold especially under the name "KSP-300®" by the company Shin-Etsu.

Additional elastomeric crosslinked organopolysiloxanes in the form of powders include cured silicone powder coated with microfine particles. These particles are described in U.S. Pat. Nos. 5,492,945, 5,756,568 and 5,945,471, the entire contents of which are hereby incorporated by reference. Suitable cured silicone powder coated with microfine particles include, but are not limited to DC9701®, available from Dow Corning.

The silicone elastomer may be present in the cosmetic composition of the present invention in an amount ranging from greater than 0% to about 95% by weight, based on the weight of the composition.

Gelling Agents

The compositions of the invention may also be optionally gelled with an oil-phase gelling agent. The gelling agent increases the liquid fatty phase viscosity and leads to a solid or flowable composition when introduced in said fatty phase. The gelling agent does not encompass waxes, in the sense that it is not waxy. The at least one gelling agent may be chosen from gelling agents in polymeric form and gelling agents in mineral form. The gelling agent may be chosen from agents that gel via chemical cross-linking and agents that gel via physical cross-linking.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34® by the company Rheox, Claytone XL®, Claytone 34® and Claytone 40® sold or made by the company Southern Clay, the modified clays known under the name quaternium-18 benzalkonium bentonites and sold or made under the names Claytone HT®, Claytone GR® and Claytone PS® by the company Southern Clay, the clays modified with stearyldimethylbenzoylammonium chloride, known as stearalkonium bentonites, such as the products sold or made under the names Claytone APA® and Claytone AF® by the company Southern Clay, and Baragel 24® sold or made by the company Rheox.

Other mineral gelling agents, which can be used in the invention, include silica, such as fumed silica. The fumed silica may have a particle size, which may be nanometric to micrometric, for example ranging from 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "Aerosil R812®" by the company Degussa and "CAB-O-SIL TS-530®" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in the composition of the present invention in an amount of from greater than 0% to 20% by weight, based on the weight of the composition.

Volatile Solvents

There may be instances where the use of a polar volatile solvent is desired. Such solvents may include, but are not limited to, alcohols, volatile esters and volatile ethers. In general, they will have a flash point below about 25° C.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

While the use of a plasticizer is not necessary in the compositions of the present invention, it may, nevertheless, be desirable. Plasticizers are organic compounds added to a high polymer both to facilitate processing and to increase the flexibility and toughness of the final product by internal modification of the polymer molecule. Examples of suitable plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa. These preservatives may be present in amounts ranging from about 0.01 to about 10% by weight, preferably from 0.5% to about 5% by weight, and more preferably from about 0.8 to about 3% by weight, based on the weight of the composition.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel® by the company Kemanord Plast or under the name Micropearl F® 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo® by the company National Starch; silicone resin microbeads such as those sold under the name Tospearl® by the company Toshiba Silicone; clays (bentone, laponite, saponite, etc.) and mixtures thereof. These fillers may be present in amounts ranging from greater than 0% to 50% by weight, based on the weight of the composition.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors. Typically, the active ingredient may be present in amounts ranging from greater than 0% to 20% by weight, based on the weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

The cosmetic compositions of the present invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol® 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

The composition of the present invention may be in the form of a liquid, semi solid such as a gel, or a solid. The cosmetic compositions may be used to make up the lips such as lip glosses or lipsticks or to make up eyelids such as eyeshadows.

The composition of the present invention may be anhydrous or non anhydrous, in the form of an aqueous emulsion, such as oil in water (O/W), water in oil (W/O), or a multiple emulsion (W/O/W, O/W/O, . . . ), or non aqueous emulsion, in which case the water is replaced with a material compatible with water, such as a diol, alcohol, glycol, polyhydric alcohol and derivatives thereof. By anhydrous, it is meant that the composition contains no added water (other than the water that may be provided by other components of the composition such as a latex or the like).

The present invention is further described in terms of the following non-limiting examples. Unless otherwise indicated, all parts and percentages are on a weight-by-weight percentage basis.

EXAMPLE

Examples 1 and 2 (Inventive Compositions) and 3 (Comparative Composition)

| PHASE | Trade Name | Ex. 1 | Ex. 2 | Comp. Ex. 3 |
|---|---|---|---|---|
| A | Kraton ® polymerG1657 M | 5.00 | 5.00 | 5.00 |
|  | Regalite ® R1100 | 10.00 | 12.00 | 10.00 |
|  | Sucrose Acetate Isobutyrate | 10.00 | 10.00 | 0.00 |
|  | Octyldodecyl Neopentanoate | 10.82 | 10.00 | 15.82 |
|  | Softisan 649 | 9.00 | 6.00 | 6.00 |
|  | DC555 | 0.00 | 3.00 | 0.00 |
|  | DC556 | 7.00 | 8.32 | 15.00 |
|  | Polyisobutene | 20.83 | 20.83 | 20.83 |
|  | Puresyn ® 150 | 5.00 | 5.00 | 5.00 |
| B | Titanium dioxide | 0.90 | 0.90 | 0.90 |
|  | D&C Red No. 7 | 1.15 | 1.15 | 1.15 |
|  | Black iron oxide | 0.25 | 0.25 | 0.25 |
|  | Red/Brown Iron Oxide | 1.55 | 1.55 | 1.55 |
|  | Octyldodecyl Neopentanoate | 5.00 | 5.00 | 5.00 |
| C | Mica | 3.50 | 2.50 | 5.00 |
| D | polyethylene wax 400 | 4.75 | 4.00 | 4.00 |
|  | polyethylene wax 500 | 5.25 | 4.50 | 4.50 |
|  | Total | 100.00 | 100.00 | 100.00 |
|  | Wear | 46 | 48 | 33 |
|  | Shine $T_0$ (Initial) | 146 | 166 | 155 |
|  | Shine $T_1$ (1 hour) | 135 | 155 | 154 |

While the comparative example exhibits a shine measurement that is not statistically different from the inventive examples, the wear values of inventive examples 1 and 2 demonstrate an improvement in the wear while maintaining a reasonable shine.

The examples were prepared as follows:

The oils of phase A were pre-heated to 100° C. for 10 minutes, with medium mixing, using a propeller mixer.

KRATON® G1675 M was added at 100° C. and mixed until totally dissolved.

Regalite® R1100 was then slowly added with medium mixing at 95° C. until the solution became homogeneous.

In a separate beaker Phase B ingredients were mixed, by hand, until the pigments were totally wet with oil to form a pigment mixture.

The pigment mixture was then transferred to a three-roll mill and milled until the colors became homogeneous to form a milled pigment mixture.

The milled pigment mixture was then transferred into a beaker containing phase A and mixed, at average speed, for approximately 5 minutes.

Phase C was then slowly added into the beaker with mixing.

Phase D was then slowly added into the beaker and mixed for 10 minutes at high speed at 100° C.

Mixing speed was then reduced and the resulting fluid transferred into individual molds at 90-95° C.

The samples contained in the molds were then cooled to 0°C-2°C in the refrigerator for 30 minutes, then were taken out of the mold and put into packages.

Inventive examples 4-7

| PHASE | Trade Name | Ex. 4 | Ex. 5 | Ex. 6 | Ex. 7 |
|---|---|---|---|---|---|
| A | Kraton ® Polymer G1657 M | 4.00 | 4.00 | 4.00 | 4.00 |
|  | Regalite ® R1100 | 4.00 | 12.00 | 16.00 | 12.00 |
|  | Sucrose Acetate Isobutyrate | 20.00 | 10.00 | 10.00 | 10.00 |
|  | Octyldodecyl Neopentanoate | 10.00 | 10.00 | 17.15 | 10.00 |
|  | Glycerine Trioctanoate | 10.00 | 10.00 | 11.00 | 6.91 |
|  | Pentaerythrityl Tetraisostearate | 2.15 | 4.15 | 0.00 | 0.00 |
|  | Softisan 649 | 5.00 | 5.00 | 0.00 | 5.00 |
|  | POLYISOBUTENE | 15.00 | 15.00 | 20.00 | 20.00 |
|  | Puresyn ® 150 | 8.00 | 8.00 | 0.00 | 5.00 |
| B | Titanium Dioxide | 0.90 | 0.90 | 0.90 | 1.40 |
|  | D&C Red No. 7 | 1.15 | 1.15 | 1.15 | 1.79 |
|  | Black Iron Oxide | 0.25 | 0.25 | 0.25 | 0.39 |
|  | Red/Brown Iron Oxide | 1.55 | 1.55 | 1.55 | 2.42 |
|  | Octyldodecyl Neopentanoate | 5.50 | 5.50 | 5.50 | 8.58 |
| C | Mica | 2.00 | 2.00 | 1.50 | 2.00 |
| D | Beeswax | 0.00 | 0.00 | 0.00 | 1.00 |
|  | Polyethylene Wax 400 | 4.50 | 4.50 | 4.50 | 4.00 |
|  | Polyethylene Wax 500 | 6.00 | 6.00 | 6.00 | 5.50 |
|  | TOTAL | 100.00 | 100.00 | 100.00 | 100.00 |
|  | Wear | 37 | 40 | 41 | 55 |
|  | Shine $T_0$ (initial) | 146 | 157 | 169 | 172 |
|  | Shine $T_1$ (1 hour) | 142 | 138 | 157 | 163 |

The wear values of inventive examples 4 through 7 demonstrate an improvement in the wear while maintaining a reasonable shine.

Shine Measurement Protocol

In order to measure the shine of the above-mentioned cosmetic product, the intensity of the light used to perform the measurement was first determined and then its reflection off the surface of the lips was measured. This was done by having a first polarizer with vertical orientation in front of the light source, and a second polarizer with vertical orientation in front of a video camera. The video camera first recorded the surface reflection along with vertical light arising from any light passing through the gloss and into the lip.

The polarizer in front of the camera was then rotated by 90 degrees (at a video rate) in order to record the intensity of any vertical light transmitted below the surface. The horizontal intensity of sub-surface transmitted light was then measured. The second, horizontal measurement was a correction accounting for any sub-surface contributions to the desired, surface signal (the gloss). The second number was then subtracted from the first to yield the shine value.

Wear Measurement Protocol

The lip compositions were applied to the lips of panelists. The lips were photographed before, and immediately after, application using diffuse lighting in a device such as the one described and claimed in US20030067545, the entire contents of which are incorporated by reference, and the images analyzed for L* color value. The L* color value indicates the darkness or intensity of the color. The panelists were then asked to eat a meal consisting of a sandwich, a salad and a hot beverage. The lips of the panelists were photographed after the meal using the device above, and the images analyzed for L* color value. The wear is reported as % wear and indicates how much of the composition remains on the lips.

Transfer Resistance Protocol

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions.

It is to be understood that the foregoing describes preferred embodiments of the invention and that modifications may be made therein without departing from the spirit or scope of the invention as set forth in the claims.

What is claimed is:

1. A method of making up lips involving applying onto the lips a composition comprising:
   (a) a block copolymer,
   (b) a tackifier,
   (c) a wax,
   (d) a liquid fatty phase comprising a volatile silicone oil, a non-volatile silicone oil, a volatile hydrocarbon oil, a non-volatile hydrocarbon oil, or a mixture of two or more thereof,
   (e) sucrose acetate isobutyrate; and
   (f) optionally, a colorant,
   wherein the composition possesses both shine and long-wear properties.

2. The method according to claim 1, wherein the block copolymer is present in an amount of from greater than 0% to about 20% by weight, based on the weight of the composition.

3. The method according to claim 1, wherein the block copolymer is a combination of di-block and tri-block copolymers of styrene-ethylene/butylene-styrene.

4. The method according to claim 1, wherein the tackifier is present in an amount of from greater than 0% to about 60% by weight, based on the weight of the composition.

5. The method according to claim 1, wherein the tackifier is a hydrogenated styrene/methyl styrene/indene copolymer.

6. The method according to claim 1, wherein the wax is present in an amount of from greater than 0% to about 40% by weight, based on the weight of the composition.

7. The method according to claim 1, wherein the liquid fatty phase is present in an amount of from greater than 0% to 80% by weight, based on the weight of the composition.

8. The method according to claim 1, wherein the sucrose acetate isobutyrate is present in an amount of from greater than 0% to 50%, based on the weight of the composition.

9. The method according to claim 1, wherein the sucrose acetate isobutyrate has a viscosity of about 100,000 cps at 30° C. and a refractive index of about 1.5 at 20° C.

10. The method according to claim 1, wherein the colorant is present in an amount effective to impart color when applied onto keratinous substrates.

11. A cosmetic composition comprising:
   (a) a block copolymer,
   (b) a tackifier,
   (c) a wax,
   (d) a liquid fatty phase comprising a volatile silicone oil, a non-volatile silicone oil, a volatile hydrocarbon oil, a non-volatile hydrocarbon oil, or a mixture of two or more thereof,
   (e) sucrose acetate isobutyrate; and
   (g) optionally, a colorant,
   wherein the composition possesses both shine and long-wear properties.

12. The composition according to claim 11, wherein the block copolymer is present in an amount of from greater than 0% to about 20% by weight, based on the weight of the composition.

13. The composition according to claim 11, wherein the block copolymer is a combination of di-block and tri-block copolymers of styrene-ethylene/butylene-styrene.

14. The composition according to claim 11, wherein the tackifier is present in an amount of from greater than 0% to about 60% by weight, based on the weight of the composition.

15. The composition according to claim 11, wherein the tackifier is a hydrogenated styrene/methyl styrene/indene copolymer.

16. The composition according to claim 11, wherein the wax is present in an amount of from greater than 0% to about 40% by weight, based on the weight of the composition.

17. The composition according to claim 11, wherein the liquid fatty phase is present in an amount of from greater than 0% to 80% by weight, based on the weight of the composition.

18. The composition according to claim 11, wherein the sucrose acetate isobutyrate is present in an amount of from greater than 0% to 50%, based on the weight of the composition.

19. The composition according to claim 11, wherein the sucrose acetate isobutyrate has a viscosity of about 100,000 cps at 30° C. and a refractive index of about 1.5 at 20° C.

20. The composition according to claim 11, wherein the colorant is present in an amount effective to impart color when applied onto keratinous substrates.

\* \* \* \* \*